United States Patent
Dembski

(10) Patent No.: US 11,275,075 B2
(45) Date of Patent: Mar. 15, 2022

(54) COLLECTION SYSTEMS FOR FLOW CYTOMETRICALLY SORTED SAMPLES AND METHODS OF USING THE SAME

(71) Applicant: Becton, Dickinson and Company, Franklin Lakes, NJ (US)

(72) Inventor: Kyle Dembski, Scotts Valley, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 161 days.

(21) Appl. No.: 16/390,376

(22) Filed: Apr. 22, 2019

(65) Prior Publication Data

US 2019/0331657 A1    Oct. 31, 2019

Related U.S. Application Data

(60) Provisional application No. 62/663,792, filed on Apr. 27, 2018.

(51) Int. Cl.
*G01N 33/487* (2006.01)
*G01N 15/14* (2006.01)
*G01N 15/10* (2006.01)

(52) U.S. Cl.
CPC ... *G01N 33/48778* (2013.01); *G01N 15/1404* (2013.01); *G01N 2015/1006* (2013.01); *G01N 2015/149* (2013.01)

(58) Field of Classification Search
CPC .......... G01N 33/4478; G01N 15/1404; G01N 2015/149
See application file for complete search history.

(56) References Cited

U.S. PATENT DOCUMENTS

| D339,194 | S | 9/1993 | Telang |
| 5,344,611 | A * | 9/1994 | Vogler ............... B01L 3/5082 422/547 |
| 7,629,113 | B2 * | 12/2009 | Seidel ............... A01K 67/027 435/2 |
| D676,567 | S | 2/2013 | Van Den Engh |

(Continued)

FOREIGN PATENT DOCUMENTS

| CN | 207051160 A1 | 2/2018 |
| EP | 0672458 A | 9/1995 |

(Continued)

OTHER PUBLICATIONS

Hawley, et al. "Flow Cytometry Protocols", Methods in Molecular Biology, 2004, vol. 263, pp. 1-424.

(Continued)

*Primary Examiner* — Michael McCullough
*Assistant Examiner* — Jessica L Burkman
(74) *Attorney, Agent, or Firm* — Bret E. Field; Bozicevic Field & Francis LLP

(57) ABSTRACT

Collection systems for flow cytometrically sorted samples are provided. Aspects of the collection systems include: a collection container having a sort tube configured to be in droplet receiving relationship with a sort block of a flow cytometer; and a sample output operatively coupling a cell collection location of the collection container to a mating connection for a receiving container, such as an evacuated receiving container. Also provided are methods using the collection systems, as well as assemblies and kits including components of the systems.

18 Claims, 6 Drawing Sheets

(56) References Cited

U.S. PATENT DOCUMENTS

| | | |
|---|---|---|
| 8,455,258 B2 | 6/2013 | Quake et al. |
| 8,727,132 B2 | 5/2014 | Miltenyi et al. |
| 8,795,500 B2 | 8/2014 | Shinoda |
| D715,925 S | 10/2014 | Suzuki |
| D717,438 S | 11/2014 | Lin |
| 9,592,483 B2* | 3/2017 | Fox .................. G05D 11/131 |
| D802,150 S | 11/2017 | Lund |
| 2002/0182738 A1 | 12/2002 | Connelly et al. |
| 2004/0025602 A1 | 2/2004 | Norton |
| 2004/0062685 A1 | 4/2004 | Norton |
| 2004/0142463 A1 | 7/2004 | Walker et al. |
| 2005/0011582 A1 | 1/2005 | Haug |
| 2005/0112541 A1* | 5/2005 | Durack .................. C12N 5/06 435/2 |
| 2011/0020855 A1 | 1/2011 | Shinoda et al. |
| 2011/0137018 A1 | 6/2011 | Chabg-Yen et al. |
| 2011/0217723 A1 | 9/2011 | Durack |
| 2011/0271746 A1 | 11/2011 | Shinoda |
| 2011/0284378 A1 | 11/2011 | Shinoda |
| 2012/0164718 A1 | 6/2012 | Bishop et al. |
| 2012/0276621 A1 | 11/2012 | Van Den Engh |
| 2013/0330739 A1 | 12/2013 | Yu |
| 2014/0078502 A1 | 3/2014 | Buchanan et al. |
| 2014/0120570 A1 | 5/2014 | Yu et al. |
| 2014/0170697 A1 | 6/2014 | Sharpe et al. |
| 2015/0010939 A1* | 1/2015 | Warner .............. G01N 35/0098 435/30 |
| 2015/0330385 A1 | 11/2015 | Lofstrom et al. |
| 2016/0041082 A1 | 2/2016 | Van Den Engh |
| 2017/0248508 A1* | 8/2017 | Ward ................. G01N 15/1404 |
| 2017/0268998 A1 | 9/2017 | Fox et al. |
| 2017/0299493 A1 | 10/2017 | Norton |

FOREIGN PATENT DOCUMENTS

| | | |
|---|---|---|
| JP | 2004500008 A | 1/1992 |
| JP | 2000516345 A | 12/2000 |
| KR | 20000053705 A | 9/2000 |
| KR | 20090096744 A | 9/2009 |
| WO | WO199004019 A1 | 4/1990 |
| WO | WO199926067 A1 | 5/1999 |
| WO | WO2010033140 A2 | 3/2010 |
| WO | WO2014047358 A1 | 3/2014 |

OTHER PUBLICATIONS

Jayasinghe et al. "Sterile and Disposable Fluidic Subsystem Suitable for Clinical High Speed Fluorescence-Activated Cell Sorting", Cytometry Part B (Clinical Cytometry) 708:344-354 (2006).

Miltenyi Biotec Gmbh, CliniMACS® Cell Separation Systems, Product Catalog 2008, 48 pages.

Miltenyi Biotec Gmbh, CliniMACS® User Manual, US Edition, Software 2.40, Jan. 2014, 128 pages.

Miltenyi Biotec Gmbh, CliniMACS® User Manual for the CliniMACS® CD34 Reagent System, Jan. 2014, 102 pages.

Sandin et al. "Magnetophoresis and cytometry with magnetic microparticles", International Congress Series, Jun. 2007, vol. 1300, pp. 271-274.

Yang et al. "Micro flow cytometry utilizing a magnetic bead-based immunoassay for rapid virus detection", Biosensors and Bioelectronics, Dec. 1, 2008, vol. 24, No. 4, pp. 855-862.

* cited by examiner

COLLECTION SYSTEMS FOR FLOW CYTOMETRICALLY SORTED SAMPLES AND METHODS OF USING THE SAME

CROSS-REFERENCE TO RELATED APPLICATION

Pursuant to 35 U.S.C. § 119(e), this application claims priority to the filing dates of U.S. Provisional Patent Application Ser. No. 62/663,792, filed Apr. 27, 2018; the disclosure of which application is incorporated herein by reference.

INTRODUCTION

A number of research and therapeutic applications require the sterile purification of living cells from a sample based on certain cell characteristics. For example, cells are often separated from a sample by cell size, shape, and surface protein expression. The isolated cells produce a homogeneous population and may be studied in the laboratory or administered to patients in various downstream, including clinical, applications. In clinical applications, living cells may be collected for use in cell therapy where the cells are introduced into the patient as treatment for an illness. Current methods for sorting and purifying cells from a sample according to their type include: single cell sorting, fluorescent activated cell sorting, magnetic cell sorting, and buoyancy activated cell sorting.

Preserving cell viability and sterility in such applications can be critical. Both cell viability and sterility may be compromised during sorting as various cell preparation and quality control steps of the sorting process may subject cells to a high stress and/or a contaminated environment. Factors that may impact cell viability during sorting include cell type, conditions of the cells prior to sorting, pressure and jet velocity at which the cells are sorted, and the buffer or medium the cells are to be sorted into. Factors that may influence the sterility of the sorted cells include the sterility of the cell sorter, the sheath fluid, and the overall system for processing the cellular sample.

SUMMARY

Collection systems for flow cytometrically sorted samples are provided. Aspects of the collection systems include: a collection container having a sort tube configured to be in droplet receiving relationship with a sort block of a flow cytometer; and a sample output operatively coupling a cell collection location of the collection container to a mating connection for a receiving container, such as an evacuated receiving container. Also provided are methods using the collection systems, as well as assemblies and kits including components of the systems.

BRIEF DESCRIPTION OF THE DRAWINGS

The invention may be best understood from the following detailed description when read in conjunction with the accompanying drawings. Included in the drawings are the following figures.

DETAILED DESCRIPTION

Figure 1:
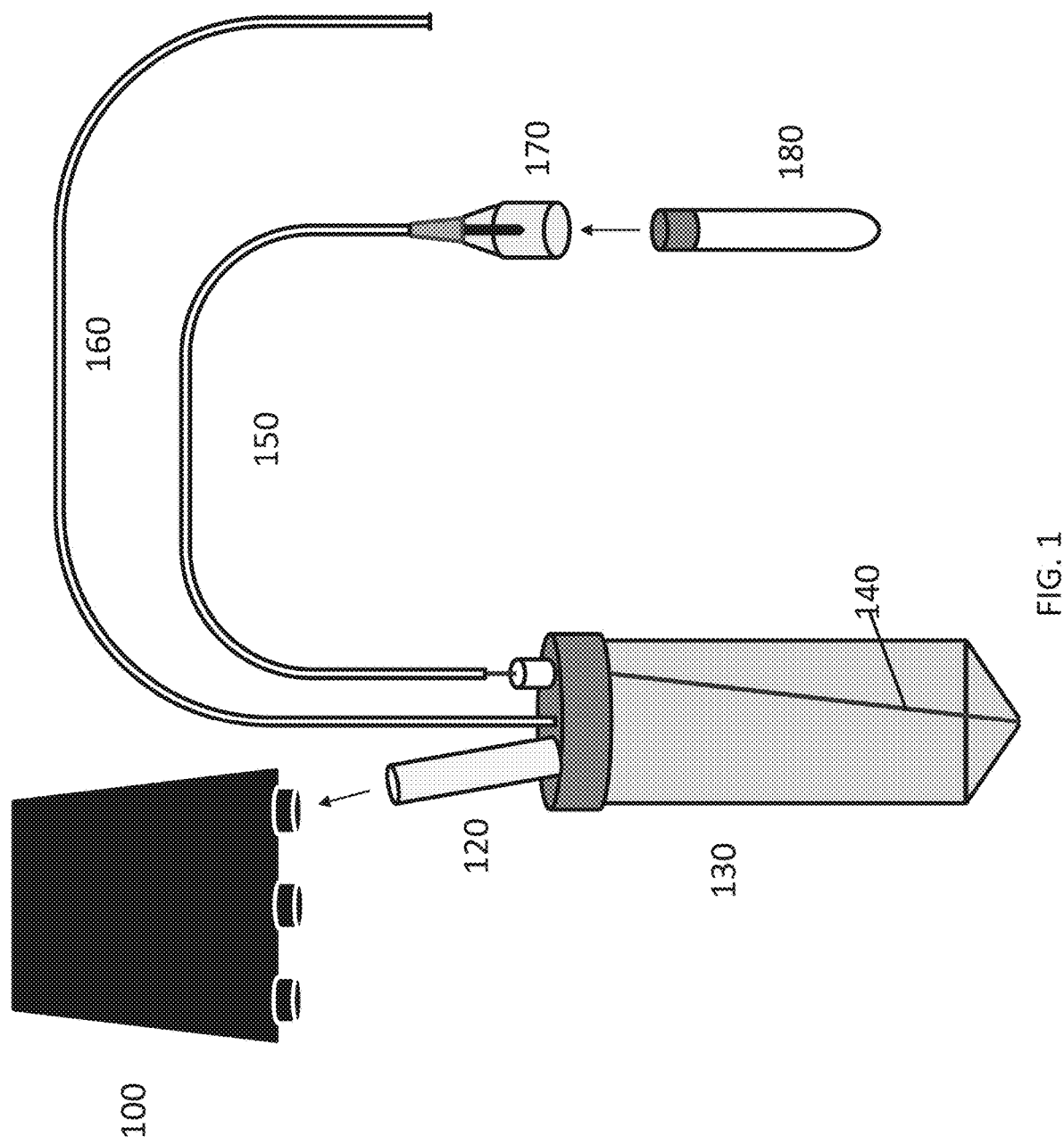
FIG. 1 provides a schematic of a collection system according to an embodiment of the invention.

Collection systems for flow cytometrically sorted samples are provided. Aspects of the collection systems include: a collection container having a sort tube configured to be in droplet receiving relationship with a sort block of a flow cytometer; and a sample output operatively coupling a cell collection location of the collection container to a mating connection for a receiving container, such as an evacuated receiving container. Also provided are methods using the collection systems, as well as assemblies and kits including components of the systems.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Collection Systems

As summarized above, aspects of the invention include collection systems for receiving flow cytometrically sorted samples from a flow cytometer. By "flow cytometrically sorted sample" is meant a composition made up of one or more cells that are the product of a flow cytometer enabled sorting process, i.e., a protocol in which cells of a sample are sorted using a flow cytometer. As such, the flow cytometrically sorted sample that may be collected by the collection systems described herein is a composition that is made up of one or more flow cytometrically sorted particles, such as flow cytometrically sorted cells. In addition to the sorted particles, the cytometrically sorted sample for which the collection systems described herein are configured may also include one more additional components, such as liquid media, etc.

The collection systems described herein may include one or more tubes or analogous receptacles configured to receive fluid, e.g., a flow cytometrically sorted sample or waste fluid, from a flow cytometer. In some instances, the one or more tubes of the collection system are configured to receive fluid from a sort block of a flow cytometer. In some cases, one or more tubes of the collection system may be fluidically coupled to one or more outlets of the sort block, where each tube may be coupled to a separate outlet. In some instances, the one or more tubes may be a sort tube, waste tube, or a capped off tube, e.g., as reviewed in greater detail below. Collection systems of the invention may have a sort tube configured to receive a flow cytometrically sorted sample from a flow cytometer. In some instances, the sort tube of the collection systems is configured to receive a flow cytometrically sorted sample from a sort block of a flow cytometer. The sort tube may receive a sample from a flow cytometer, e.g., the sort block of a flow cytometer, and direct the received sample to a collection container. In some cases, the sort tube guides a flow cytometrically sorted sample to a collection container in a manner that minimizes contact between the flow cytometrically sorted sample and various inner surfaces, e.g., walls, of the collection container. During use, the sort tube may be configured to so as to reduce, if not eliminate, sorted stream contact with an inner surface of the sort tube, such as where the longitudinal axis of the sort tube is aligned with the longitudinal axis of the sorted stream. The sort tube may be coupled to, e.g., attached to, the collection container or may be an integrated component of the collection container. The sort tube may be positioned at any suitable position relative to the surfaces of the collection container; for example, the sort tube may be positioned at the top surface of the collection container, on the side surfaces of the collection container, or at the bottom surface of the collection container. The sort tube may have any convenient shape or structure; for example, the sort tube may be a tube, cone, funnel, etc. The sort tube may have any convenient dimensions. In some cases, the sort tube ranges from 5 cm to 25 cm in length; for example, the sort tube may range from 5 cm to 20 cm in length, from 5 cm to 15 cm in length, or from 5 cm to 10 cm in length. In some cases, the sort tube has an inner diameter ranging from 1 mm to 25 mm; for example, the sort tube may have a diameter ranging from 1 mm to 20 mm, from 1 mm to 15 mm, or from 1 mm to 10 mm. The sort tube may include a guide at an end distal to the sort block. The guide may be of any suitable shape; for example, the guide may be conical or cylindrical. In some cases, the guide is configured as an expanding cone; for example, the guide may be a cone having walls that expand outwards from the center of the cone. In some cases, the guide ranges from 5 cm to 25 cm in length; for example, the guide may range from 5 cm to 20 cm in length, from 5 cm to 15 cm in length, or from 5 cm to 10 cm in length.

In some cases, the collection systems described herein include a waste tube configured to receive waste fluid from the flow cytometer. In some instances, the waste tube of the collection systems is configured to receive a waste fluid from a sort block of a flow cytometer. The waste tube may receive waste fluid from a flow cytometer, e.g., the sort block of a flow cytometer, and direct the waste fluid to a waste location, e.g., a waste container. The waste tube may have any convenient shape or structure; for example, the waste tube may be a tube, cone, funnel, etc. The waste tube may have any convenient dimensions. In some cases, the waste tube ranges from 5 cm to 25 cm in length; for example, the sort tube may range from 5 cm to 20 cm in length, from 5 cm to 15 cm in length, or from 5 cm to 10 cm in length. In some cases, the waste tube has an inner diameter ranging from 1 mm to 25 mm; for example, the waste tube may have a diameter ranging from 1 mm to 20 mm, from 1 mm to 15 mm, or from 1 mm to 10 mm.

In some cases, the collection systems described herein include a capped off tube. The tube may be capped off such that flow of fluid through the tube is blocked. The tube may be capped off to maintain sterility of the system and promote fluid flow through other tubes coupled to the sort block such as, e.g., a sort tube and waste tube. The capped off tube may be coupled to an outlet of a sort block at a first end and sealed at a second end. The second end of the tube may be sealed by any suitable cap or lid. Alternatively, any sealing cover may be employed in such instances to cover an outlet of the sort block, e.g., to maintain sterility thereof, where alternative sealing covers include caps, lids, etc.

The sort tube and guide components, such as described above, may be fabricated from any convenient materials, including those materials detailed below.

The collection systems described herein may further include a collection container. The collection container may receive and collect a flow cytometrically sorted sample from a flow cytometer. As described above, the collection container may have a sort tube in droplet receiving relationship with a flow cytometer, such as a sort block of a flow cytometer. In some cases, the collection container may be directly coupled to an outlet of the sort block of the flow cytometer; e.g., a container without a sort tube may be directly attached to an outlet of a sort block of a flow cytometer. The collection container may provide a sterile environment for collecting the flow cytometrically sorted cellular product. By sterile environment is meant an environment that is free or substantially free from live bacteria or other microorganisms. The collection container of the system may have any suitable configuration for collection of flow cytometrically sorted samples. In some cases, the container has a volume ranging from 1 mL to 100 mL; for example, the volume of the container may range from 1 mL to 90 mL, from 1 mL to 80 mL, from 1 mL to 70 mL, from 1 mL to 60 mL, from 1 mL to 50 mL, from 1 mL to 40 mL, from 1 mL to 30 mL, from 1 mL to 20 mL, or from 1 mL to 10 mL. In some cases, the container has a volume that is 200 mL or less such as, e.g., 150 mL or less, 100 mL or less, 80 mL or less, 70 mL or less, 60 mL or less, 50 mL or less, 40 mL or less, 30 mL or less, 20 mL or less or 10 mL or less.

The collection container may have rigid or pliant walls, as desired. In some cases, the collection container includes one or more rigid components, e.g., walls, where the one or more rigid components define the container. By "rigid" is meant that the components, e.g., walls, are unable to bend or be forced out of shape, such that they are not flexible. In such instances, the container may have any convenient configuration. In some instances of such embodiments, the collection container is configured as a tube. While the dimensions of the tube in such instances may vary, in some instances the tube has a largest inner diameter ranging from 10 to 100 mm, such as 25 to 75 mm. Where the containers include a rigid component, the containers may be fabricated from any convenient material. Any suitable material that is compatible with a fluidic sample (e.g., biological sample) may be employed, including metal, glass (e.g., Pyrex glass, borosilicate glass), ceramic or plastic. In certain embodiments, the container is formed from a plastic, such as a rigid plastic, polymeric or thermoplastic material. For example, suitable plastics may include, but are not limited to polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In certain embodiments, the particle sorting module housing is formed from a polyester, where polyesters of interest may include, but are not limited to poly(alkylene terephthalates) such as poly (ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(ε-caprolactone) and poly(β-propiolactone); poly(alkylene isophthalates) such as poly(ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly (trans-1,4-cyclohexanediyl ethylene dicarboxylate); poly(1, 4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly (tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide); polyesters, e.g., polyethylene terephthalates, e.g., Mylar™ polyethylene terephthalate; etc.

In some cases, the collection container is a pliant container, such as a bag. By "pliant" is meant that the collection container may be bent or flexed from its original shape without any significant structural changes, such as tearing, cracking, perforating, etc. For example, a pliant sample container may be flexed and/or deformed from its original shape, while still maintaining a sealed barrier preventing contact between a fluid inside the sample container and the surrounding environment. In some cases, the pliant container is made from a flexible material that has a Young's modulus of 1 GPa or less, such as 0.7 GPa or less, including 0.5 GPa or less, for instance, 0.3 GPa or less, or 0.1 GPa or less, such as 0.05 GPa or less, or 0.01 GPa or less. In some cases, the collection container is configured as a bag. In these instances, the pliant collection containers may be fabricated from any convenient material. Containers of interest include containers that are Ethinyl Vinyl Acetate (EVA) based, such as EVA freezing bag, such as a CRYOCYTE™ freezing bag (Baxter Healthcare Corporation, Deerfield, Ill.), CELL-FREEZE® cryogenic freezing bag (Charter Medical, Winston-Salem, N.C.), ORIGEN CRYOSTORE™ freezing bag (OriGen BioMedical, Austin, Tex.), and the like.

Where desired, the collection container may have a cell collection location. By "cell collection location" is meant a location within the collection container for receiving, collecting, and/or storing a flow cytometrically sorted sample. The cell collection location may be positioned at any suitable location within the collection container. For example, where the collection container is a tube, such as described above, the tube may include a bottom defining the cell collection location. The bottom of the tube may be any shape suitable for collecting droplets of flow cytometrically sorted sample, e.g., from the sort block of the flow cytometer. In some instances, the tube has a flat or rounded bottom. In some instances, the bottom of the tube includes a conical bottom defining the cell collection location. In some instances, the bottom of the tube includes a cylindrical bottom defining the cell collection location. The cell collection location may hold any convenient volume of sample. In some cases, the cell collection location may hold a volume of sample ranging from 1 mL to 50 mL, from 1 mL to 25 mL, from 1 mL to 15 mL, or from 1 mL to 10 mL. As indicated above, the cell collection location may have any suitable shape for collecting a flow cytometrically sorted cellular product; for example, the cell collection location may be conical, cylindrical, flat, rounded, etc.

In certain embodiments, a collection container of the system may include a sample output. The sample output may operatively couple a cell collection location of the collection container to a mating connection for an evacuated receiving container, e.g., as described in further detail below. In some cases, the sample output includes a fluidic line, e.g., for transporting a flow cytometrically sorted cellular product from a cell collection location of the collection container to an evacuated receiving container. Where desired, the output may provide for sterile transport of the sample. The fluidic line may have any suitable configuration; for example, the fluidic line may be a tubular fluidic line. In some cases, the fluidic line is a rigid fluidic line. In certain embodiments, the fluidic line is a pliant, i.e., flexible, fluidic line. The sample output fluidic line may be made of any suitable material, where such materials include, but are not limited to, those described above with respect to the container. The sample output fluidic line may have any convenient length. In some cases, the length of the sample output fluidic line ranges from 5 cm to 50 cm, such as, e.g., from 5 cm to 40 cm, from 5 cm to 30 cm, from 5 cm to 20 cm, or from 5 cm to 10 cm. The sample output fluidic line may have any convenient diameter. In some cases, the inner diameter of the sample output fluidic line ranges from 1 mm to 20 mm such as, e.g., from 1 mm to 15 mm, from 1 mm to 10 mm, from 1 mm to 5 mm, or from 1 mm to 2 mm.

In some cases, the sample output fluidic line includes a first end configured to operatively couple to a cell collection location of a collection container and a second end including a mating connection for an evacuated receiving container, such that a flow cytometrically sorted sample may flow from the cell collection location through the sample output and to an evacuated receiving container. The flow cytometrically sorted sample may enter the sample output at the first, proximal end of the sample output, which proximal end may be coupled to the cell collection location. The flow cytometrically sorted sample may exit the sample output at a second, distal end of the sample output. The second, i.e., distal, end of the sample output may include a mating connection. In some cases, the sample output includes one or more ends that are sealed or welded to another component, e.g., the container, the mating connection, etc. In some cases, a first end of the sample output has a welded connection with the collection container, e.g., the first end may be welded to the collection container. In some cases, a second end of the sample output has a welded connection with the mating connection, e.g., the second end may be welded to the mating connection. In some cases, the second end of the sample output includes a plurality of mating connections.

The mating connection is a connection configured to operatively, e.g., fluidically, couple the distal end of the sample output to an evacuated receiving container. In certain embodiments, the mating connection is an integrated structure of the sample output; for example, the mating connection has a welded connection with the sample output, e.g., the mating connection is welded to an end, e.g., the distal end, of the sample output. The mating connection may couple the sample output to an evacuated receiving container. The mating connection may provide a sterile connection between an end of the sample output and the evacuated receiving container. In some cases, the mating connection includes a piercing member operatively connected to the sample output, e.g., the sample output fluidic line. In some cases, the piercing member is a rigid structure that extends from one end of the sample output such as, e.g., a hollow needle joined to an end of a sample output fluidic line. The piercing member may attach the mating connection to an evacuated receiving container, e.g., by piercing a surface of the evacuated receiving container, such as a septum of the evacuated receiving container. In some cases, the piercing member may be inserted in the evacuated receiving container after the piercing member has pierced a surface of the evacuated receiving container. In some cases, a flow cytometrically sorted cellular product may flow from the cell collection location of the collection container, through a sample output fluidic line, and through a piercing member to an evacuated receiving container. The mating connection may include a single-ended piercing member or piercing member having a single exposed end, e.g., for piercing a surface of the evacuated receiving container. In some cases, the mating connection for coupling the sample output to an evacuated receiving container includes a tubular member operatively connected to the sample output. The tubular member may connect to or receive a needle of a syringe, as described in detail below. In some cases, the tubular member is configured to ensure an airtight connection when a needle of the syringe is inserted in the tubular member. A flow cytometrically sorted cellular product may flow from the cell collection location of the collection container, through a sample output fluidic line, and through the tubular member to the syringe. In some cases, the sample output includes a plurality of mating connections that couple the sample output to one or more evacuated receiving containers. The sample output may include at least one mating connection having a piercing member, as described above, and at least one mating connection having a tubular member, as described above. In some cases, the sample output includes a connector, e.g., a Y connector, having at least two mating connections where each mating connection may be separately coupled to an evacuated receiving container. In some cases, the at least two mating connections include piercing members for attaching to evacuated receiving containers, e.g., vacutubes. In some cases, the at least two mating connections include tubular members for connecting with or receiving needles of evacuated receiving containers, e.g., syringes. In some cases, at least one mating connection of the connector includes a piercing member and at least one other mating connection of the connector includes a tubular member.

As described above, the system may include an evacuated receiving container. In certain embodiments, the evacuated receiving container is, during use, operatively coupled to the mating connection, e.g., by a piercing member. The evacuated receiving container may be configured to receive a flow cytometrically sorted cellular product from the cell collection location of the collection container via a sample output and mating connection. An "evacuated receiving container" refers to a container including an evacuated interior volume. In some cases, the evacuated receiving container is a container including an evacuated interior volume and an opening sealed by a septum. In some cases, the evacuated receiving container is an air evacuated, hermetically sealed tube container for receiving a sample. The evacuated receiving container may be any suitable air evacuated sterile container such as, e.g., an evacuated blood collection tube or a vacutube. In some cases, the evacuated receiving container is a container including an evacuated interior volume and an opening sealed by a plunger. In some cases, the evacuated receiving container is a syringe having a needle for receiving a sample and a barrel housing a plunger that may be pushed or pulled. The evacuated receiving container may be made of any suitable material such as, but not limited to, polycarbonate, polyethylene, polypropylene, polyethylene-terephthalate, polystyrene, impact modified polystyrene, glass, etc. The evacuated receiving container may have any convenient volume ranging, e.g., from 1 ml to 15 ml, from 1 ml to 10 ml, from 1 ml to 5 ml, or from 1 ml to 2 ml. In certain instances, evacuated receiving containers of interest include BD Vacutainer® blood collection tubes. Suitable evacuated receiving containers are described in, e.g., U.S. Pat. Nos. 5,344,611; 5,326,535; 5,320,812; 5,257,633; and 5,246,666, the disclosures of which are incorporated herein by reference. In certain embodiments, evacuated receiving containers of interest include syringes. Suitable evacuated receiving containers are described in, e.g., U.S. Pat. No. 2,756,748, the disclosures of which are incorporated herein by reference. In some cases, the system includes a plurality of evacuated receiving containers. The evacuated receiving containers may be coupled to a plurality of sample outputs, each sample output having at least one mating connection that may be coupled to each evacuated receiving container.

The system may further include a media input fluidically coupled to the collection container, e.g., via a welded connection, such as described above, e.g., for transport of media to or from the interior of the collection container. The media input may deliver an amount of a liquid medium to the collection container. In some cases, the media output includes a fluidic line. The fluidic line may have any suitable configuration; for example, the fluidic line may be a tubular fluidic line. In some cases, the fluidic line is a rigid fluidic line. In certain embodiments, the fluidic line is a flexible fluidic line. In some cases, the media input includes one or more ends that are sealable or weldable; for example, a first end of the media input may have a welded connection with the collection container, e.g., the first end may be welded to the collection container. The media input fluidic line may have any convenient length. In some cases, the length of the media input fluidic line ranges from 5 cm to 50 cm, such as, e.g., from 5 cm to 40 cm, from 5 cm to 30 cm, from 5 cm to 20 cm, or from 5 cm to 10 cm. The media input fluidic line may have any convenient diameter. In some cases, the diameter of the media input fluidic line ranges from 1 mm to 20 mm such as, e.g., from 1 mm to 15 mm, from 1 mm to 10 mm, from 1 mm to 5 mm, or from 1 mm to 2 mm. In some cases, the system includes a plurality of media inputs. In certain embodiments, the media input has a second end coupled to a media source, e.g., a media supply container. In such instances, the media supply container includes a liquid medium, where the nature of the liquid medium may vary. Examples of liquid media that may be present in the media supply container include, but are not limited to: cell nutrient media, cell preservative media, etc.

As indicated above, any of the fluidic connections with respect to the collection system, e.g., within the collection system and/or between the collection system and other components, e.g., media supply containers, etc., may be made using sterile tube welding, as desired. Any convenient sterile tube welding system and materials may be employed.

The collection systems having been generally described above, six specific embodiments are now reviewed in greater detail in connection with figures thereof. In the embodiments depicted in FIGS. 1-6, a collection system includes a collection container integrated with a VACUTAINER® blood collection tube (Becton Dickinson, Franklin Lakes, N.J.) and/or a syringe. The method uses the vacuum of the VACUTAINER® blood collection tube and/or syringe to decrease cell recovery loss by providing adequate vacuum pull on the sample in the collection container. Multiple VACUTAINER® blood collection tubes and/or syringes can be used to fully remove an entire sample from the sort vessel with minor fluid losses in the system.

FIG. 1 shows a schematic of a sterile collection system according to an embodiment of the invention. A sort block 100 of a cell sorter delivers sorted cells as a sorted particle stream into a collection container that is a collection tube 130. A sort tube 120 can be coupled to an outlet of the sort block and guide the sorted particle stream to the collection tube 130. The straight sort tube 120 connecting to the collection tube 130 minimizes the chance for cells to contact the walls of the collection tube 130 when sorted. In addition, the longitudinal axis of the sort tube is aligned with the longitudinal axis of the sorted particle stream so as to minimize contact of particles, e.g., cells in the sorted particle stream with an inner surface of the sort tube. By minimizing contact of sorted cells with the walls of the sort tube and/or collection tube 130 prior to falling into media at the bottom of the sort collection tube, cell loss is decreased and cell viability is increased. The straight sort tube 120 minimizes the possibility of sample building up within the sort collection tube 130 prior to landing in media at the bottom of the sort collection tube 130, which increases cell viability and decreases cell recovery loss. The sorted cells are collected in the conical bottom of sort collection tube 130. A media input tube 160 is coupled to the sort collection tube 130. The media input tube 160 may be joined to the sort collection tube 130 via a welded connection. A PEEK tube 140 is inserted inside the sort collection tube 130. A first end of the PEEK tube 140 is positioned at the conical bottom of the sort collection tube 130 where sorted cells are collected. The second end of the PEEK tube 140 meets a first end of a sample output tube 150. The second end of the sample output tube 150 includes a mating element 170 configured to fluidically couple the interior of output tube 150 to the interior of a VACUTAINER® blood collection tube 180. The mating element 170 can be welded or sealed to the second end of the sample output tube 150. The mating element 170 includes a needle for piercing the septum of the VACUTAINER® blood collection tube 180. After the VACUTAINER® blood collection tube 180 has been connected to the mating element 170, an aliquot of sorted cells are drawn into the VACUTAINER® blood collection tube 180.

Figure 2:
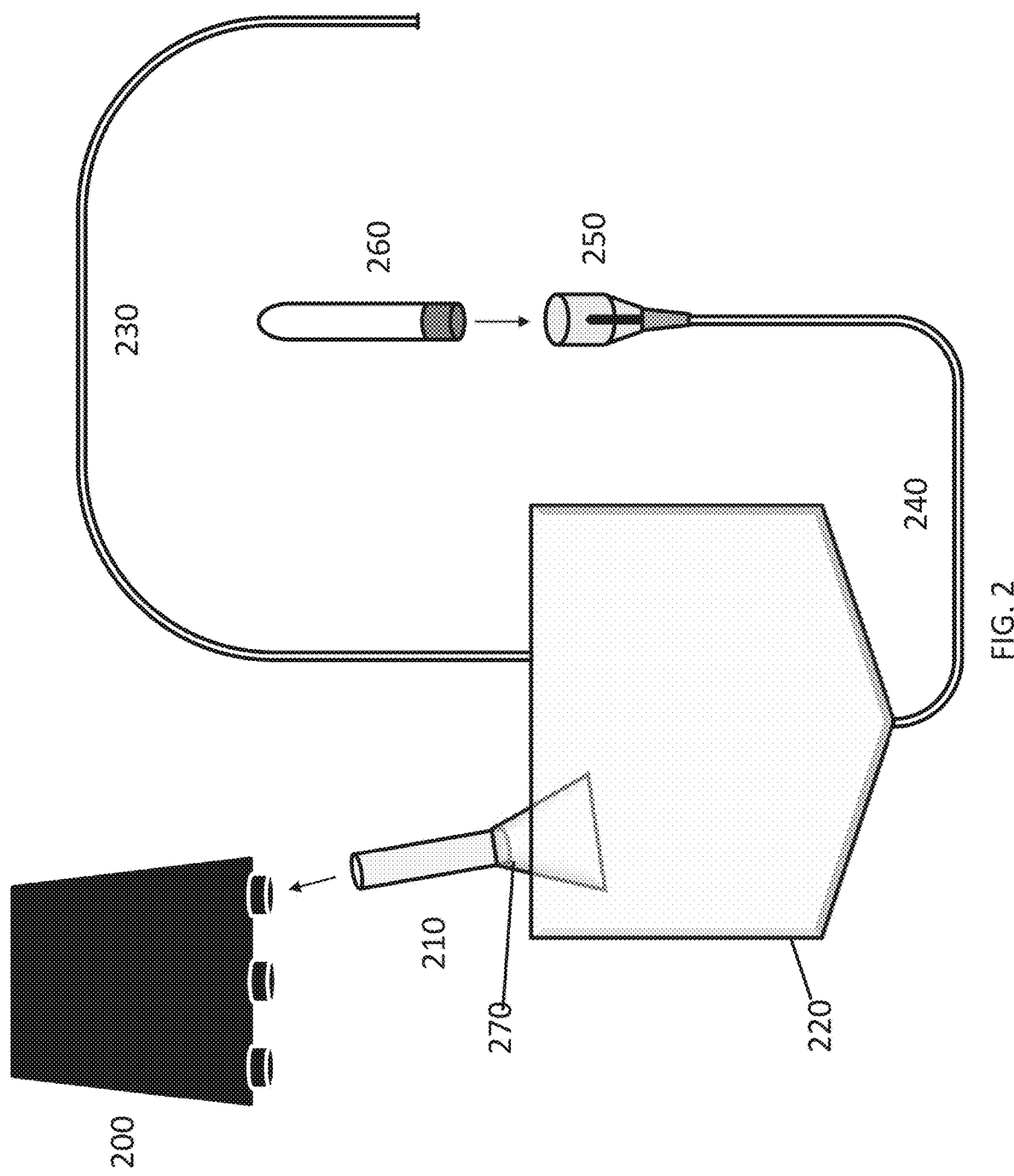
FIG. 2 provides a schematic of an embodiment of a collection system according to an embodiment of the invention.

FIG. 2 shows a schematic of the sterile collection system according to another embodiment of the invention. A sort block 200 of a cell sorter delivers sorted cells into a collection container that is a collection bag 220. A sort tube 210 may be coupled to an outlet of the sort block and guide the sorted cells to the collection bag 220. The sort tube has an expanding cone 270 positioned at the end of the sort tube distal from the sort block 200. The straight sort tube 210 and expanding cone 270 connecting to the collection bag 220 minimize the chance for cells to contact the walls of the collection bag 220 when sorted. In addition, the longitudinal axis of the sort tube is aligned with the longitudinal axis of the sorted particle stream so as to minimize contact of particles, e.g., cells in the sorted particle stream with an inner surface of the sort tube. By minimizing sorted cells contacting the walls of the sort tube and/or collection bag 220 prior to falling into media at the bottom of the bag, cell loss is decreased and cell viability is increased. The straight sort tube 210 and expanding cone 270 minimize the possibility of sample building up within the collection bag 220 prior to landing in media at the bottom of the collection bag 220, which increases cell viability and decreases cell recovery loss. The cells may be collected at the bottom of the collection bag 220. The collection bag 220 contains an integrated cone design used to help the cells fall into the bottom of the bag to minimize cell loss. A media input tube 230 may be coupled to the collection bag 220. The media input tube 230 may be joined to the collection bag 220 via a welded connection. A sample output tube 240 may be joined to the collection bag 220. A first end of the sample output tube 240 may be joined to the collection bag 220 via a welded connection. The second end of the sample output tube 240 includes a mating element 250 configured to fluidically couple the interior of output tube 240 to the interior of a VACUTAINER® blood collection tube 260. The mating element 250 can be welded or sealed to the second end of the sample output tube 240. The mating element 240 includes a needle for piercing the septum of the VACUTAINER® blood collection tube 260. After the VACUTAINER® blood collection tube 260 has been connected to the mating element 250, an aliquot of sorted cells are drawn into the VACUTAINER® blood collection tube 260.

Figure 3:
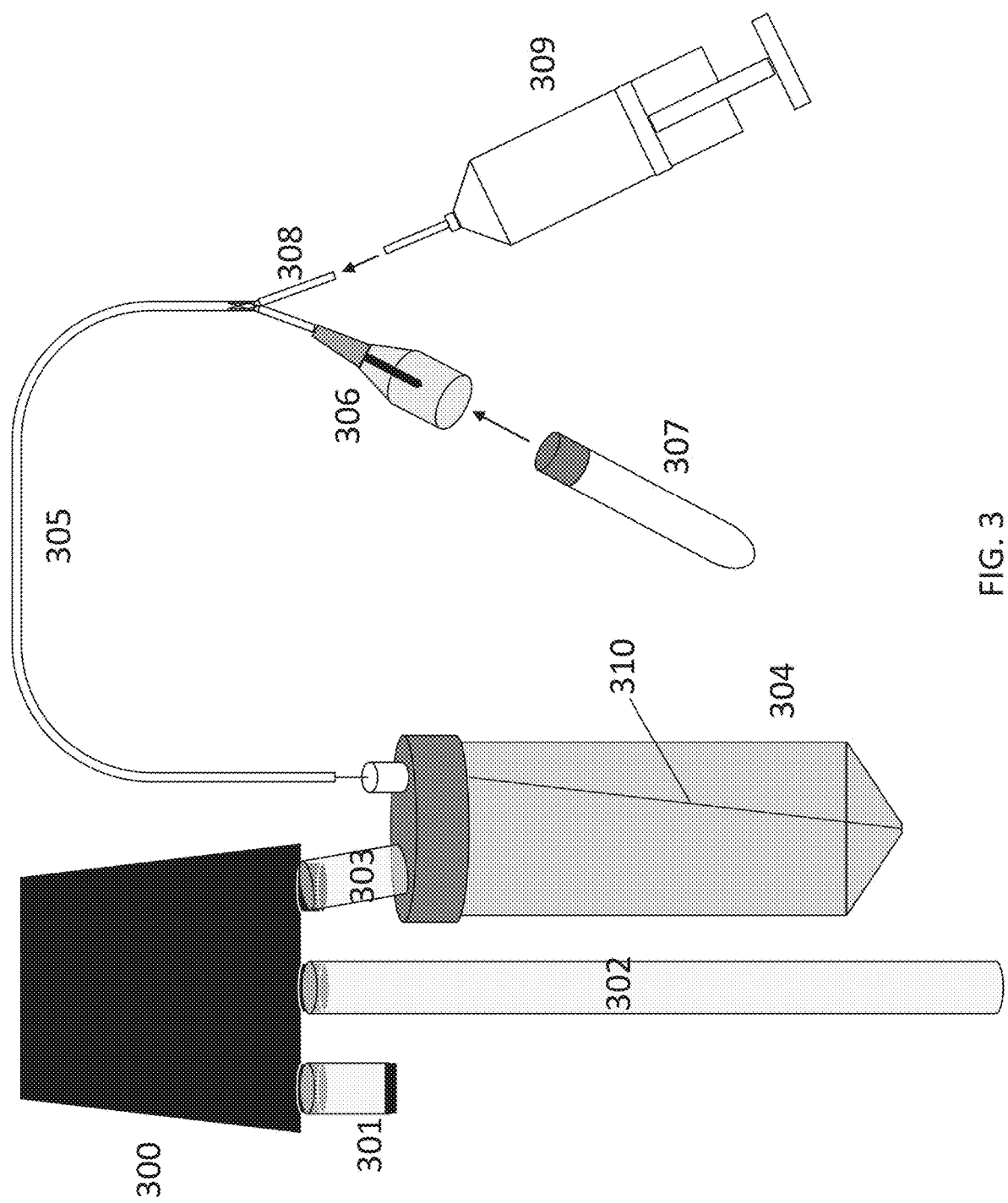
FIG. 3 provides a schematic of a collection system according to an embodiment of the invention.

FIG. 3 shows a schematic of a sterile collection system according to an embodiment of the invention. A sort block 300 of a cell sorter delivers sorted cells as a sorted particle stream into a collection container that is a collection tube 304. A sort tube 303 can be coupled to an outlet of the sort block and guide the sorted particle stream to the collection tube 304. A waste line 302 is coupled to a second outlet of the sort block, and the sort block 300 delivers waste fluid to the waste line 302. A capped off tube 301 is coupled to a third outlet of sort block 300. Instead of a capped off tube, the opening may be covered by a simple cap or lid. The straight sort tube 303 connecting to the collection tube 304 minimizes the chance for cells to contact the walls of the collection tube 304 when sorted. In addition, the longitudinal axis of the sort tube is aligned with the longitudinal axis of the sorted particle stream so as to minimize contact of particles, e.g., cells in the sorted particle stream with an inner surface of the sort tube. By minimizing contact of sorted cells with the walls of the sort tube 303 and/or collection tube 304 prior to falling into media at the bottom of the sort collection tube, cell loss is decreased and cell viability is increased. The straight sort tube 303 minimizes the possibility of sample building up within the sort collection tube 304 prior to landing in media at the bottom of the sort collection tube 304, which increases cell viability and decreases cell recovery loss. The sorted cells are collected in the conical bottom of sort collection tube 304. A PEEK tube 310 is inserted inside the sort collection tube 304. A first end of the PEEK tube 310 is positioned at the conical bottom of the sort collection tube 304 where sorted cells are collected. The second end of the PEEK tube 310 meets a first end of a sample output tube 305. The second end of the sample output tube 305 includes one or both of two mating elements 306 and 308. Mating element 306 is configured to fluidically couple the interior of output tube 305 to the interior of a VACUTAINER® blood collection tube 307. The mating element 306 can be welded or sealed to the second end of the sample output tube 305. The mating element 306 includes a needle for piercing the septum of the VACUTAINER® blood collection tube 307. After the VACUTAINER® blood collection tube 307 has been connected to the mating element 306, an aliquot of sorted cells is drawn into the VACUTAINER® blood collection tube 307. Mating element 308 is configured to fluidically couple the interior of output tube 305 to the interior of a syringe 309. The mating element 308 can be welded or sealed to the second end of the sample output tube 305. The mating element 308 includes a tube for connecting to or receiving the needle of the syringe 309. After the syringe 309 has been connected to the mating element 308, an aliquot of sorted cells can be drawn into the syringe 309. Where desired, either of the outlets of mating element 308 may be sealed if not in use, e.g., to maintain sterility of the system.

Figure 4:
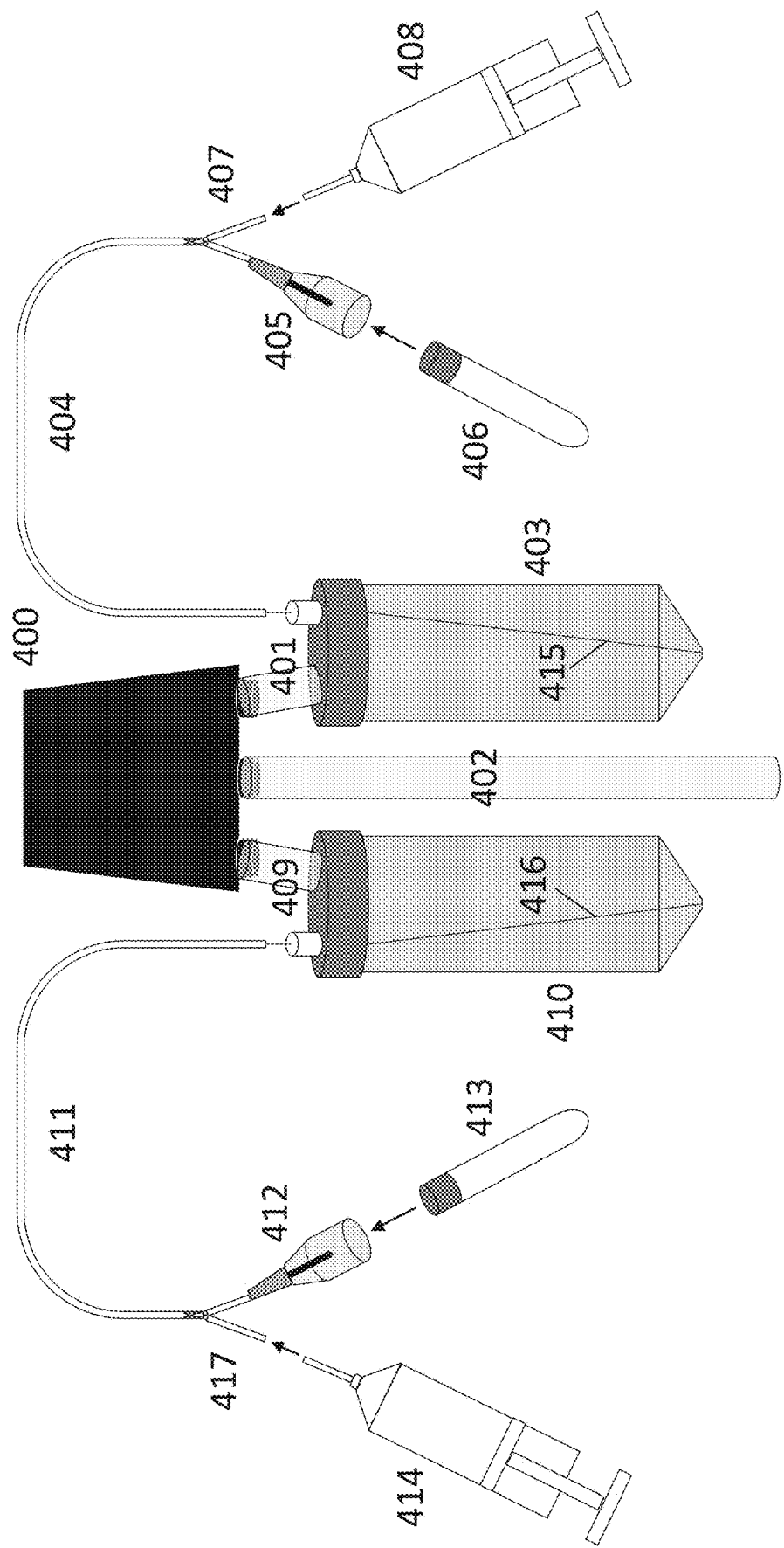
FIG. 4 provides a schematic of a collection system according to an embodiment of the invention.

FIG. 4 shows a schematic of a sterile collection system according to another embodiment of the invention. A sort block 400 of a cell sorter delivers sorted cells as a sorted particle stream into two collection containers that are collection tubes 403 and 410, where each tube receives sorted cells in a sorted particle stream from a separate outlet of the sort block, e.g., a first outlet and a second outlet. Sort tubes 401 and 409 can be coupled to outlets of the sort block, e.g., a first outlet and a second outlet, respectively, and guide the sorted particle streams to the collection tubes 403 and 410, respectively. A waste line 402 is coupled to an outlet of the sort block 400, e.g., a third outlet, and the sort block 400 delivers waste fluid to the waste line 402. The straight sort tubes 401 and 409 connecting to the collection tubes 403 and 410, respectively, minimize the chance for cells to contact the walls of the collection tubes 403 and 410 when sorted. In addition, the longitudinal axis of each sort tube is aligned with the longitudinal axis of the sorted particle stream so as to minimize contact of particles, e.g., cells in the sorted particle stream, with an inner surface of the sort tube. By minimizing contact of sorted cells with the walls of the sort tubes 401 and 409 and/or collection tubes 403 and 410 prior to falling into media at the bottom of the sort collection tubes, cell loss is decreased and cell viability is increased. The straight sort tubes 401 and 409 minimize the possibility of sample building up within the sort collection tubes 403 and 410 prior to landing in media at the bottom of the sort collection tubes, which increases cell viability and decreases cell recovery loss. The sorted cells are collected in the conical bottoms of sort collection tubes 403 and 410. PEEK tubes 415 and 416 are inserted inside the sort collection tubes 403 and 410. A first end of the PEEK tubes 415 and 416 are positioned at the conical bottom of the sort collection tubes 403 and 410 where sorted cells are collected. The second end of the PEEK tubes 415 and 416 meet a first end of sample output tubes 404 and 411. The second end of the sample output tube 404 includes one or both of two mating elements 405 and 407. The second end of the sample output tube 411 includes one or both of two mating elements 412 and 417. Mating elements 405 and 412 are configured to fluidically couple the interior of output tubes 404 and 411 to the interior of a VACUTAINER® blood collection tube 406 and 413. The mating elements 405 and 412 can be welded or sealed to the second ends of the sample output tubes 404 and 411. The mating elements 405 and 412 include a needle for piercing the septum of the VACUTAINER® blood collection tubes 406 and 413. After the VACUTAINER® blood collection tubes 406 and 413 have been connected to the mating elements 405 and 412, an aliquot of sorted cells is drawn into the VACUTAINER® blood collection tubes 406 and 413. Mating elements 407 and 417 are configured to fluidically couple the interior of output tubes 404 and 411 to the interior of syringes 408 and 414. The mating elements 407 and 417 can be welded or sealed to the second end of the sample output tubes 404 and 411. The mating elements 407 and 417 each include a tube for connecting to or receiving the needle of the syringes 408 and 414. After syringes 408 and 414 have been connected to the mating elements 407 and 414, respectively, an aliquot of sorted cells is drawn into each of syringes 408 and 414. Where desired, either of the outlets of mating elements 407 and 414 may be sealed if not in use, e.g., to maintain sterility of the system.

Figure 5:
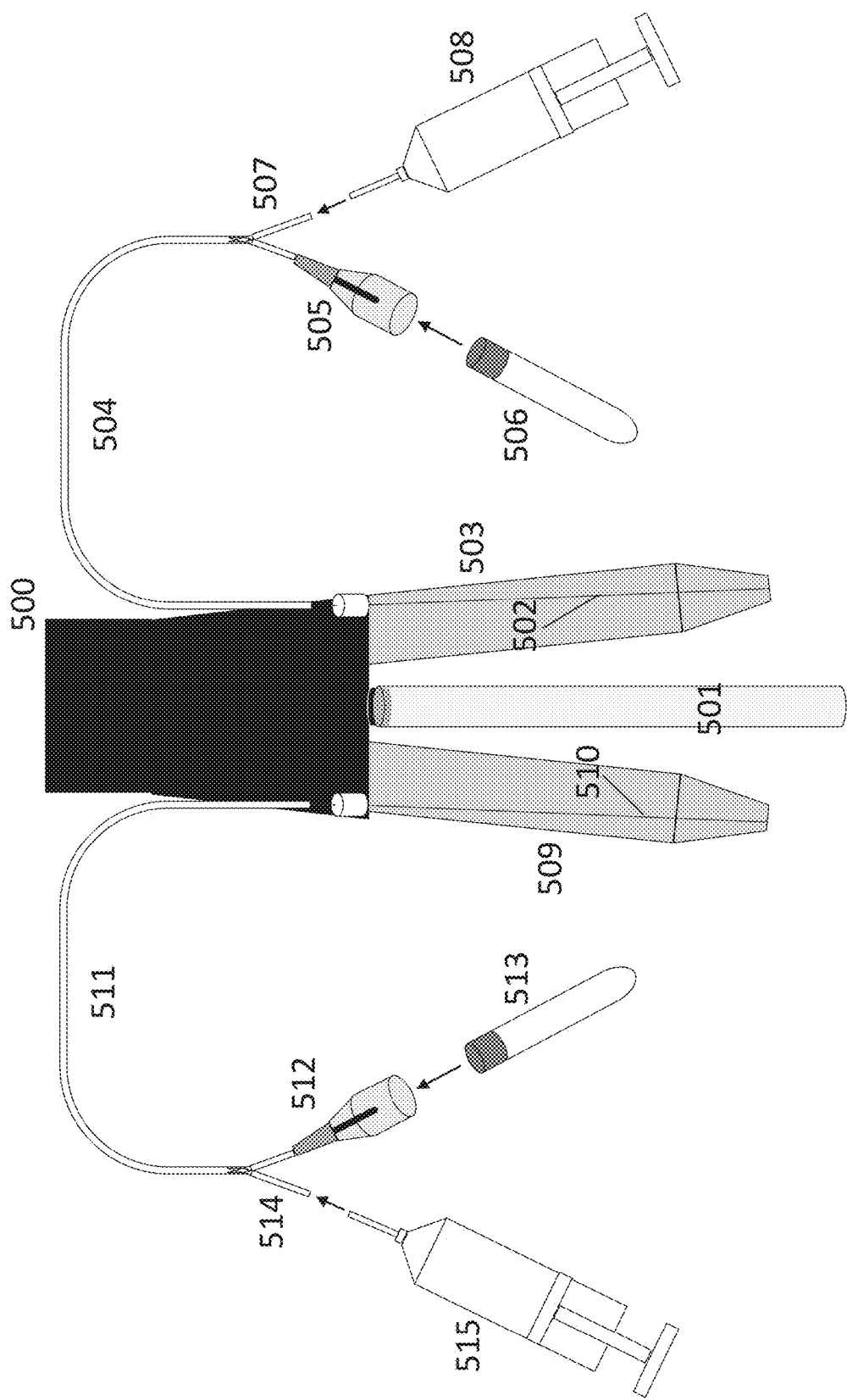
FIG. 5 provides a schematic of a collection system according to an embodiment of the invention.

FIG. 5 shows a schematic of a sterile collection system according to another embodiment of the invention. A sort block 500 of a cell sorter delivers sorted cells as a sorted particle stream into two collection containers that are collection tubes 503 and 509, where each tube receives sorted cells in a sorted particle stream from a separate outlet of the sort block, e.g., a first outlet and a second outlet. Collection tubes 503 and 509 can be coupled to outlets of the sort block, e.g., a first outlet and a second outlet, respectively, and guide the sorted particle streams to the bottom of the collection tubes. The collection tubes 503 and 509 are directly attached to the sort block. A waste line 501 is coupled to an outlet of the sort block 500, e.g., a third outlet, and the sort block 500 delivers waste fluid to the waste line 501. The sorted cells are collected in the conical bottoms of sort collection tubes 503 and 509. PEEK tubes 502 and 510 are inserted inside the sort collection tubes 503 and 509. A first end of the PEEK tubes 502 and 510 are positioned at the conical bottom of the sort collection tubes 503 and 509 where sorted cells are collected. The second end of the PEEK tubes 502 and 510 meet a first end of sample output tubes 504 and 511. The second end of the sample output tube 504 includes one or both of two mating elements 505 and 507. The second end of the sample output tube 511 includes one or both of two mating elements 512 and 514. Mating elements 505 and 512 are configured to fluidically couple the interior of output tubes 504 and 511 to the interior of a VACUTAINER® blood collection tube 506 and 513. The mating elements 507 and 514 can be welded or sealed to the second ends of the sample output tubes 504 and 511. The mating elements 505 and 512 include a needle for piercing the septum of the VACUTAINER® blood collection tubes 506 and 513. After the VACUTAINER® blood collection tubes 506 and 513 have been connected to the mating elements 505 and 512, an aliquot of sorted cells are drawn into the VACUTAINER® blood collection tubes 506 and 513. Mating elements 507 and 514 are configured to fluidically couple the interior of output tubes 504 and 511 to the interior of syringes 508 and 515. The mating elements 507 and 514 can be welded or sealed to the second end of the sample output tubes 504 and 511. The mating elements 507 and 514 each include a tube for connecting to or receiving the needle of syringes 508 and 515. After syringes 508 and 515 have been connected to the mating element 507 and 514, an aliquot of sorted cells is drawn into each of the syringes 508 and 515. Where desired, either of the outlets of mating elements 507 and 514 may be sealed if not in use, e.g., to maintain sterility of the system.

Figure 6:
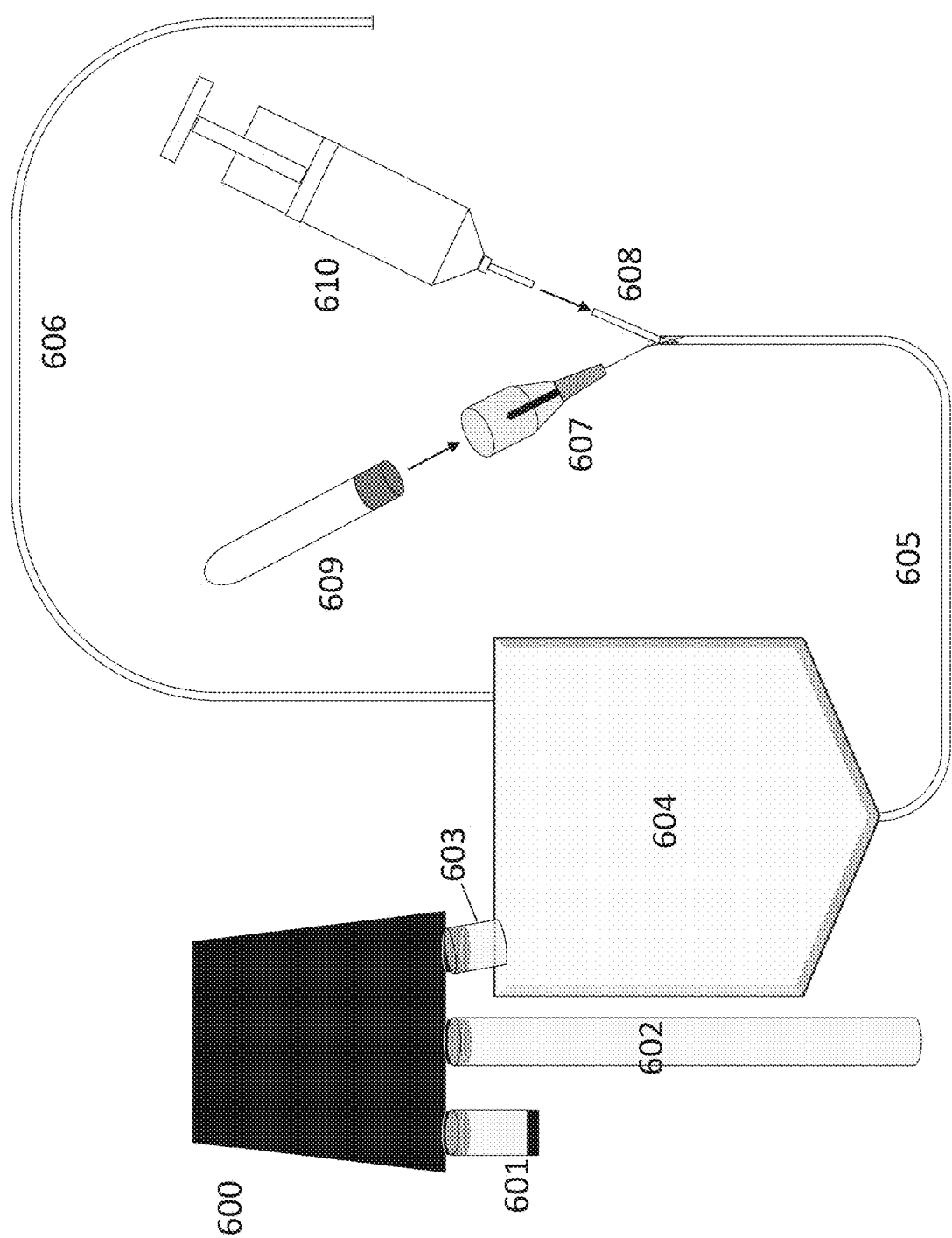
FIG. 6 provides a schematic of a collection system according to an embodiment of the invention.

FIG. 6 shows a schematic of the sterile collection system according to another embodiment of the invention. A sort block 600 of a cell sorter delivers sorted cells into a collection container that is a collection bag 604. A sort tube 603 may be coupled to an outlet of the sort block and guide the sorted cells to the collection bag 604. A waste line 602 is coupled to a second outlet of the sort block, and the sort block 600 delivers waste fluid to the waste line 602. A capped off tube 601 is coupled to a third outlet of sort block 600. The straight sort tube 603 connecting to the collection bag 604 minimize the chance for cells to contact the walls of the collection bag 604 when sorted. In addition, the longitudinal axis of the sort tube is aligned with the longitudinal axis of the sorted particle stream so as to minimize contact of particles, e.g., cells in the sorted particle stream with an inner surface of the sort tube. By minimizing sorted cells contacting the walls of the sort tube 603 and/or collection bag 604 prior to falling into media at the bottom of the bag, cell loss is decreased and cell viability is increased. The straight sort tube 603 minimizes the possibility of sample building up within the collection bag 604 prior to landing in media at the bottom of the collection bag 604, which increases cell viability and decreases cell recovery loss. The cells may be collected at the bottom of the collection bag 604. The collection bag 604 contains an integrated cone design used to help the cells fall into the bottom of the bag to minimize cell loss. A media input tube 606 may be coupled to the collection bag 604. The media input tube 606 may be joined to the collection bag 604 via a welded connection. A sample output tube 605 may be joined to the collection bag 604. A first end of the sample output tube 605 may be joined to the collection bag 604 via a welded connection. The second end of the sample output tube 605 includes one or both of two mating elements 607 and 608. Mating element 607 is configured to fluidically couple the interior of output tube 605 to the interior of a VACUTAINER® blood collection tube 609. The mating element 607 can be welded or sealed to the second end of the sample output tube 605. The mating element 607 includes a needle for piercing the septum of the VACUTAINER® blood collection tube 609. After the VACUTAINER® blood collection tube 609 has been connected to the mating element 607, an aliquot of sorted cells are drawn into the VACUTAINER® blood collection tube 609. Mating element 608 is configured to fluidically couple the interior of output tube 605 to the interior of a syringe 610. The mating element 608 can be welded or sealed to the second end of the sample output tube 605. The mating element 608 includes a tube for connecting to or receiving the needle of the syringe 610. After the syringe 610 has been connected to the mating element 608, an aliquot of sorted cells is drawn into the syringe 610. Where desired, either of the outlets of mating element 608 may be sealed if not in use, e.g., to maintain sterility of the system.

Flow Cytometer Systems

Aspects of the invention further include flow cytometer systems, where the flow cytometer systems include a sorting flow cytometer operatively coupled to a collection system, e.g., as described above. Flow-type particle sorting systems, such as sorting flow cytometers, are used to sort particles in a fluid sample based on at least one measured characteristic of the particles. In a flow-type particle sorting system, particles, such as molecules, analyte-bound beads, or individual cells, in a fluid suspension are passed in a stream by a detection region in which a sensor detects particles contained in the stream of the type to be sorted. The sensor, upon detecting a particle of the type to be sorted, triggers a sorting mechanism that selectively isolates the particle of interest.

Particle sensing typically is carried out by passing the fluid stream by a detection region in which the particles are exposed to irradiating light, from one or more lasers, and the light scattering and fluorescence properties of the particles are measured. Particles or components thereof can be labeled with fluorescent dyes to facilitate detection, and a multiplicity of different particles or components may be simultaneously detected by using spectrally distinct fluorescent dyes to label the different particles or components. Detection is carried out using one or more photosensors to facilitate the independent measurement of the fluorescence of each distinct fluorescent dye.

One type of flow-type particle sorting system is the electrostatic sorting type. In an electrostatic sorter, a fluid suspension is jetted from a nozzle and vibrated to break the stream into uniform discrete drops. The sorting mechanism includes a drop charging means connected to the stream to charge drops containing a particle of the type to be sorted with an electrical charge as it breaks off from the jet stream. The stream of drops is passed through a transverse electrostatic field established by a pair of oppositely charged deflection plates. Charged drops containing a particle of the type to be sorted are deflected in a direction and in an amount related to the polarity and magnitude of the drop charge and are collected in distinct collection receptacles. Uncharged drops are not deflected passing through the electrostatic field and are collected by a central receptacle.

Various aspects of sorting flow cytometers are described in U.S. Pat. No. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference in their entirety. In some instances, the sorting flow cytometer is a Becton Dickinson cell sort, such as the BD Biosciences Influx™ cell sorter, BD Biosciences FACSAria™ III and BD FACSAria™ Fusion cell sorters, BD Biosciences FACSJazz™ cell sorter, the BD Biosciences FACSMelody™ cell sorter, and the like.

In some cases, the flow cytometer includes a sort block. The sort block may be configured to deliver a sorted sample to a collection container, e.g., as described above. As described above, the collection container may have a sort tube in droplet receiving relationship with the sort block; for example, the sort tube may receive a flow cytometrically sorted cellular product, e.g., in the form of droplets, from the sort block and guide the flow cytometrically sorted cellular product to the collection container. In some cases, the sort block delivers a sorted sample to a sort tube with a first end coupled to an opening of the sort block and a second end coupled to the collection container. The sort block may be any sort block known in the art such as, e.g., the sort block described in U.S. Pat. No. 6,880,414, the disclosure of which is herein incorporated by reference in its entirety.

Of interest in certain embodiments is a sterile cell sorter having sterile, single use, particle sorting module. In such instances, the particle sorting modules include an enclosed housing having an aligner for coupling the housing with a particle sorting system, a flow cell nozzle positioned at the proximal end of the housing, a sample interrogation region in fluid communication with the orifice of the flow cell nozzle, a droplet deflector and a sort block. The term "enclosed" means that each component of the particle sorting module is fully contained within the housing and the components are sealed off or isolated from the ambient environment. In other words, the components within the enclosed housing are not exposed to or have no contact with the outside environment. In some embodiments, the components contained within the housing are isolated from the gaseous environment of the ambient environment (i.e., are not exposed to the gases outside of the housing). In other embodiments, the components contained within the housing are isolated from the fluidic environment of the ambient environment (i.e., are not exposed to any fluids present outside of the housing). In yet other embodiments, the components contained within the housing are sterile and are isolated from live bacteria or other microorganisms that are present in the ambient environment (i.e., sterile). Further details regarding such sorting flow cytometers are provided in PCT patent application no. PCT/US2017/024609 published as WO 2017/180325; the disclosure of which is herein incorporated by reference.

A given flow cytometer system may be operatively coupled to a single collection system, or multiple collection systems. As such, a given system may have multiple sort tubes coupled to the sort block of the flow cytometer; for example, a system may include at least 1, at least 2, at least 3, at least 4, or at least 5 sort tubes. In certain embodiments, the system includes a plurality of sort tubes, each sort tube having a guide at an end distal to the sort block. In some cases, the system of the present disclosure includes a plurality of collection containers; for example, the system can include at least 1 collection container, at least 2 collection containers, at least 3 collection containers, at least 4 collection containers, or at least 5 collection containers. Each of the plurality of collection containers may include a sort tube for receiving a flow cytometrically sorted cellular product from a sort block of a flow cytometer.

Methods

Aspects of the disclosure also include methods for sorting particles of an initial sample, such as cells in a biological sample. Methods according to certain embodiments include irradiating an initial sample containing particles in a flow stream in an interrogation region of a flow cell, such as a flow cell of a particle sorting module, detecting light (e.g., fluorescent light) from the sample, and sorting the particles of the sample into a collection system, e.g., as described above. In certain embodiments, the sample is a biological sample and methods include sorting and collecting at least one type of cell.

In some embodiments, the initial sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

Cells of interest may be targeted for separation from the flow stream according to a variety of parameters, such as a phenotypic characteristic identified via the attachment of a particular fluorescent label to cells of interest. In some embodiments, the system is configured to deflect analyzed droplets that are determined to include a target cell. A variety of cells may be targeted for sorting using the subject methods. Target cells of interest include, but are not limited to, stem cells, T cells, dendritic cells, B Cells, granulocytes, leukemia cells, lymphoma cells, virus cells (e.g., HIV cells) NK cells, macrophages, monocytes, fibroblasts, epithelial cells, endothelial cells, and erythroid cells. Target cells of interest include cells that have a convenient cell surface marker or antigen that may be captured or labelled by a convenient affinity agent or conjugate thereof. For example, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71. In some embodiments, the target cell is selected from HIV containing cell, a Treg cell, an antigen-specific T-cell populations, tumor cells or hematopoetic progenitor cells (CD34+) from whole blood, bone marrow or cord blood.

In practicing the subject methods, an amount of an initial fluidic sample is injected into the flow cytometer. The amount of sample injected into the particle sorting module may vary, for example, ranging from 0.001 mL to 1000 mL, such as from 0.005 mL to 900 mL, such as from 0.01 mL to 800 mL, such as from 0.05 mL to 700 mL, such as from 0.1 mL to 600 mL, such as from 0.5 mL to 500 mL, such as from 1 mL to 400 mL, such as from 2 mL to 300 mL and including from 5 mL to 100 mL of sample.

Methods according to embodiments of the present disclosure include counting and sorting labeled particles (e.g., target cells) in a sample. In practicing the subject methods, the fluidic sample including the particles is first introduced into a flow nozzle of the system. Upon exit from the flow nozzle, the particles are passed substantially one at a time through the sample interrogation region where each of the particles is irradiated to a source of light and measurements of light scatter parameters and, in some instances, fluorescent emissions as desired (e.g., two or more light scatter parameters and measurements of one or more fluorescent emissions) are separately recorded for each particle. The particles are passed in the flow stream substantially one at a time in a flow path through the sample interrogation region in the particle sorting module where each particle is illuminated by a light source. Depending on the properties of the flow stream being interrogated, 0.001 mm or more of the flow stream may be irradiated with light, such as 0.005 mm or more, such as 0.01 mm or more, such as 0.05 mm or more, such as 0.1 mm or more, such as 0.5 mm or more and including 1 mm or more of the flow stream may be irradiated with light. In certain embodiments, methods include irradiating a planar cross-section of the flow stream in the sample interrogation region, such as with a laser (as described above). In other embodiments, methods include irradiating a predetermined length of the flow stream in the sample interrogation region, such as corresponding to the irradiation profile of a diffuse laser beam or lamp.

In certain embodiments, methods including irradiating the flow stream at or near the flow cell nozzle orifice. For example, methods may include irradiating the flow stream at a position about 0.001 mm or more from the nozzle orifice, such as 0.005 mm or more, such as 0.01 mm or more, such as 0.05 mm or more, such as 0.1 mm or more, such as 0.5 mm or more and including 1 mm or more from the nozzle orifice. In certain embodiments, methods include irradiating the flow stream immediately adjacent to the flow cell nozzle orifice.

In series with a sensing region, detectors, such as photomultiplier tubes (or "PMT"), are used to record light that passes through each particle (in certain cases referred to as forward light scatter), light that is reflected orthogonal to the direction of the flow of the particles through the sensing region (in some cases referred to as orthogonal or side light scatter) and fluorescent light emitted from the particles, if it is labeled with fluorescent marker(s), as the particle passes through the sensing region and is illuminated by the energy source. Each of forward light scatter (or FSC), orthogonal light scatter (SSC), and fluorescence emissions (FL1, FL2, etc.) include a separate parameter for each particle (or each "event"). Thus, for example, two, three or four parameters can be collected (and recorded) from a particle labeled with two different fluorescence markers.

Suitable light detecting protocols, include but are not limited to optical sensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, light from the irradiated flow stream at the sample interrogation region of the particle sorting module is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, light is measured with a charge-coupled device (CCD). Where the light from the irradiated flow stream at the sample interrogation region of the particle sorting module is measured with a CCD, the active detecting surface area of the CCD may vary, such as from 0.01 cm2 to 10 cm2, such as from 0.05 cm2 to 9 cm2, such as from, such as from 0.1 cm2 to 8 cm2, such as from 0.5 cm2 to 7 cm2 and including from 1 cm2 to 5 cm2.

The data recorded for each particle is analyzed in real time or stored in a data storage and analysis means, such as a computer, as desired. U.S. Pat. No. 4,284,412 describes the configuration and use of a flow cytometer of interest equipped with a single light source while U.S. Pat. No. 4,727,020 describes the configuration and use of a flow cytometer equipped with two light sources.

In certain embodiments, the particles are detected and uniquely identified by exposing the particles to excitation light and measuring the fluorescence of each particle in one or more detection channels, as desired. Fluorescence emitted in detection channels used to identify the particles and binding complexes associated therewith may be measured following excitation with a single light source, or may be measured separately following excitation with distinct light sources. If separate excitation light sources are used to excite the particle labels, the labels may be selected such that all the labels are excitable by each of the excitation light sources used.

Methods in certain embodiments also include data acquisition, analysis and recording, such as with a computer, wherein multiple data channels record data from each detector for the light scatter and fluorescence emitted by each particle as it passes through the sample interrogation region of the particle sorting module. In these embodiments, analysis includes classifying and counting particles such that each particle is present as a set of digitized parameter values. The subject systems may be set to trigger on a selected parameter in order to distinguish the particles of interest from background and noise. "Trigger" refers to a preset threshold for detection of a parameter and may be used as a means for detecting passage of a particle through the light source. Detection of an event that exceeds the threshold for the selected parameter triggers acquisition of light scatter and fluorescence data for the particle. Data is not acquired for particles or other components in the medium being assayed which cause a response below the threshold. The trigger parameter may be the detection of forward scattered light caused by passage of a particle through the light beam. The flow cytometer then detects and collects the light scatter and fluorescence data for the particle.

A particular subpopulation of interest is then further analyzed by "gating" based on the data collected for the entire population. To select an appropriate gate, the data is plotted so as to obtain the best separation of subpopulations possible. This procedure may be performed by plotting forward light scatter (FSC) vs. side (i.e., orthogonal) light scatter (SSC) on a two dimensional dot plot. A subpopulation of particles is then selected (i.e., those cells within the gate) and particles that are not within the gate are excluded. Where desired, the gate may be selected by drawing a line around the desired subpopulation using a cursor on a computer screen. Only those particles within the gate are then further analyzed by plotting the other parameters for these particles, such as fluorescence. Where desired, the above analysis may be configured to yield counts of the particles of interest in the sample.

In certain embodiments, the system operates to determine a timeslot during which one or more collection systems are aligned with the deflected droplet receiving location, e.g., the output of a sort block of the flow cytometer. In some instances, the deflection signal includes an initial deflection sub-signal and a final deflection sub-signal; and the system operates to produce the deflection signal by sending an initial deflection sub-signal at the beginning of the timeslot that configures the deflector to deflect an analyzed droplet, when present. In certain cases, methods include sending a final deflection sub-signal to the particle sorting module at the end of the timeslot that configures the deflector not to deflect an analyzed droplet. In some embodiments, methods include sending a final deflection sub-signal to the particle sorting module after a single analyzed droplet has been deflected during the timeslot, where the final deflection sub-signal configures the deflector not to deflect an analyzed droplet.

Sorted particles, e.g., cells, of interest are collected by the collection system, e.g., as described above. As such, aspects of the method may include operatively coupled a collection system to a flow cytometer, e.g., to be in receiving relationship with the output, such as a sort block, of the flow cytometer.

In certain embodiments, the method includes operatively coupling an evacuated receiving container to the mating connection of a collection system. The evacuated receiving container may be coupled to the mating connection after a piercing member of the mating connection of a sample output pierces a surface of the evacuated receiving container; for example, the piercing member of the mating connection may puncture a lid or cap of the receiving container such that the piercing member is inserted into the evacuated receiving container. After the evacuated receiving container is coupled to the mating connection, the flow cytometrically sorted sample may be pulled or drawn from the cell collection location of the collection container through the sample output into the evacuated receiving container by the vacuum in the evacuated receiving container. In some cases, the evacuated receiving container is a syringe, and the syringe may be coupled to the mating connection after the needle of the syringe is inserted into a tubular member of the mating connection. In some cases, the flow cytometrically sorted sample may be pulled or drawn from the cell collection location of the collection container through the sample output into the evacuated receiving container by the vacuum in the evacuated receiving container, e.g., that may be created by pulling a plunger of the syringe. A given method may include coupling only a single evacuated container to the mating connection, or a sequentially coupling two or more evacuated containers to the mating end, as desired.

In some cases, the method further includes introducing a liquid medium into the collection container, e.g., via the fluidically coupled media input. The liquid medium may be introduced into the collection container at any time, e.g., before or after the liquid cellular sample has been sorted, before or after the flow cytometrically sorted cellular product is delivered to the cell collection location of the collection container, before or after the flow cytometrically sorted cellular product is removed from the cell collection location, etc. Suitable liquid media for introducing into the collection container include, but are not limited to, cell nutrient media, cell preservative media, etc., such as described above. The volume of liquid medium introduced may have a volume of 50 mL or less, 40 mL or less, 30 mL or less, 20 mL or less, or 10 mL or less.

Aspects of the methods may further include producing a container enclosing an interior volume comprising a flow cytometrically sorted sample. In some cases, the methods include producing a container enclosing an interior volume comprising a flow cytometrically sorted sample and including an opening sealed by a septum, e.g., a VACUTAINER® blood collection tube having an amount of flow cytometrically sorted cells present therein. In certain embodiments, the methods include producing a syringe having an amount of flow cytometrically sorted cells present therein. The container may provide a sterile environment for the flow cytometrically sorted sample. The container may be an evacuated receiving container that has received a volume of a flow cytometrically sorted sample, e.g., from the collection container. In some cases, the flow cytometrically sorted sample is a sterilely sorted sample, e.g., a sorted sample produced by a cell sorter, e.g., as described above. The container may contain any volume of flow cytometrically sorted sample. The volume of flow cytometrically sorted sample may be 10 mL or less, 5 mL or less, 2 mL or less, or 1 mL or less. The cytometrically sorted sample can contain $10^{11}$ cells or less, $10^{10}$ cells or less, $10^9$ cells or less, $10^8$ cells or less, $10^7$ cells or less, $10^6$ cells or less, $10^5$ cells or less, $10^4$ cells or less, $10^3$ cells or less, 500 cells or less, 100 cells or less, 10 cells or less, or one cell per milliliter. Because the sample present in the container is a flow cytometrically sorted sample, the sample may include, in addition to the one or more sorted cells of interest, other components introduced via the sorting process, e.g., cellular labels, such as fluorescent labels, sheath fluid components, cell nutrient media components, cell preservative components, etc.

Utility

Systems and methods as described herein find use in a variety of applications where it is desirable to analyze and sort particle components in a sample in a fluid medium, such as a biological sample, and then store sorted products, e.g., for later use, such as therapeutic use. Embodiments of the invention find use in providing increased sterility to particle sorting systems which enhances collection of samples of greater purity as well as reduces incidences of cross-contamination between analyzed samples, such as in research and high throughput laboratory testing.

Embodiments of the invention find use in applications where cells prepared from a biological sample may be desired for research, laboratory testing or for use in therapy. In some embodiments, the subject methods and devices may facilitate obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems may facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

Embodiments of the invention provide for closed sorting devices and methods, which may reduce, if not eliminate, one or more of: risk of contamination of the sample be processed; risk of exposure of operators to sample components, which may be important in situations where biohazardous samples are being processed; etc.

The flow cytometrically sorted samples produced using systems and methods as described here may be administered to a subject in a cell therapy protocol or any application where the infusion of a sterile volume of live cells into a subject is desired. Conditions that may be treated by the administration of the flow cytometrically sorted sample include, but are not limited to, blood disorders, immune system disorders, organ damage, etc.

As such, the systems and methods described herein may find use in cell therapy protocols. A cell therapy protocol is a protocol in which viable cellular material including, e.g., cells and tissues, may be prepared and introduced into a subject as a therapeutic treatment. A typical cell therapy protocol may include the following steps: sample collection, cell isolation, genetic modification, culture and expansion in vitro, cell harvesting, sample volume reduction and washing, biopreservation, storage, and introduction of cells into a subject. The protocol may begin with the collection of viable cells and tissues from source tissues of a subject to produce a sample of cells and/or tissues. The sample may be collected via any suitable procedure that includes, e.g., administering a cell mobilizing agent to a subject, drawing blood from a subject, removing bone marrow from a subject, etc. After collecting the sample, cell enrichment may occur via several methods including, e.g., centrifugation based methods, filter based methods, elutriation, magnetic separation methods, fluorescence-activated cell sorting (FACS), and the like. In some cases, the enriched cells may be genetically modified by any convenient method, e.g., nuclease mediated gene editing. The genetically modified cells can be cultured, activated, and expanded in vitro. In some cases, the cells are preserved, e.g., cryopreserved, and stored for future use where the cells are thawed and then administered to a patient, e.g., the cells may be infused in the patient.

Kits

Aspects of the present disclosure also include kits including any combination of components of the systems and assemblies, e.g., as described above. In some instances, the kits include a) an assembly comprising: 1) a collection container having a sort tube configured to be positioned in droplet receiving relationship with a sort block of a flow cytometer; and 2) a sample output operatively coupling a cell collection location of the collection container to a mating connection for an evacuated receiving container; and b) an evacuated receiving container, e.g., a VACUTAINER® blood collection tube or a syringe. In some instances, the kits include at least one collection container that may be directly coupled to an outlet of a sort block of a flow cytometer. In some instances, the kits include a waste tube for coupling to an outlet of a sort block. In certain embodiments, the kits include a tube cap or lid for capping an opening of a tube coupled to a sort block. Suitable collection containers, sort tubes, sample outputs, mating connections, and evacuated receiving containers are described above in detail. The kits may include a plurality of any of the containers, tubes, outputs, mating connections, and components described above. Where desired, the kits may further include one or more additional components that find use in an application, e.g., reagents, buffers, etc. Any or all of the kit components may be present in sterile packaging, as desired.

In addition to the above-mentioned components, a subject kit may further include instructions for using the components of the kits, e.g., to practice the subject methods. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., a portable flash drive, CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A flow cytometer system, the system comprising:
   a) a sorting flow cytometer comprising an electrostatic droplet deflector for producing a flow cytometrically sorted sample;
   b) a collection container having a sort tube in droplet receiving relationship with the sorting flow cytometer, wherein the sort tube is configured to receive the flow cytometrically sorted sample from the sorting flow cytometer and direct the received flow cytometrically sorted sample to the collection container;
   c) a fluidic line operatively coupling a cell collection location at the bottom of the collection container to a mating connection for a receiving container; and
   d) an evacuated receiving container operatively coupled to the mating connection, wherein the evacuated receiving container has a vacuum that draws from the collection location via the fluidic line;
   wherein the system is sterile.

2. The system according to claim 1, wherein the collection container comprises rigid walls.

3. The system according to claim 2, wherein the collection container is configured as a tube.

4. The system according to claim 3, wherein the tube comprises a conical bottom defining the cell collection location.

5. The system according to claim 4, wherein the fluidic line comprises a tube located in the collection container.

6. The system according to claim 1, wherein the collection container comprises flexible walls.

7. The system according to claim 6, wherein the collection container is configured as a bag.

8. The system according to claim 7, wherein the fluidic line comprises a tube located outside of the collection container.

9. The system according to claim 1, wherein the sort tube comprises a guide.

10. The system according to claim 9, wherein the guide is configured as an expanding cone.

11. The system according to claim 1, wherein the fluidic line comprises a tubular fluidic line.

12. The system according to claim 1, wherein the mating connection comprises a piercing member or tubular member operatively connected to the fluidic line.

13. The system according to claim 1, wherein the system further comprises a media input fluidically coupled the collection container.

14. The system according to claim 1, wherein the system comprises a welded connection.

15. A method comprising:
   flow cytometrically processing a sample with a flow cytometer system comprising:
   a) a flow cytometer having a sort block and an electrostatic droplet deflector;
   b) a collection container having a sort tube in droplet receiving relationship with the sort block, wherein the sort tube is configured to receive a flow cytometrically sorted sample from the flow cytometer and direct the received flow cytometrically sorted sample to the collection container;
   c) a fluidic line operatively coupling a cell collection location at the bottom of the collection container to a mating connection for a receiving container; and
   d) an evacuated receiving container operatively coupled to the mating connection, wherein the evacuated receiving container has a vacuum that draws from the collection location via the fluidic line;
   wherein the system is sterile.

16. The method according to claim 15, wherein the flow cytometrically processing comprises sorting one or more types of cells from the sample.

17. The method according to claim 16, wherein the one or more types of cells comprises cells useful in cell therapy applications.

18. An assembly comprising:
   a) a collection container having a sort tube configured to be positioned in droplet receiving relationship with a sort block and an electrostatic droplet deflector of a flow cytometer, wherein the sort tube is configured to receive a flow cytometrically sorted sample from the flow cytometer and direct the received flow cytometrically sorted sample to the collection container;
   b) a sample output fluidic line operatively coupling a cell collection location at the bottom of the collection container to a mating connection for a receiving container; and
   c) an evacuated receiving container operatively coupled to the mating connection, wherein the evacuated receiving container has a vacuum that draws from the collection location via the fluidic line;
   wherein the assembly is sterile.

* * * * *